United States Patent [19]

Frizzell

[11] Patent Number: 4,921,489
[45] Date of Patent: May 1, 1990

[54] HYPODERMIC NEEDLE SHIELD

[76] Inventor: John B. H. Frizzell, Box 938, Didsbury, Alberta, Canada, T0M 0W0

[21] Appl. No.: 221,869

[22] Filed: Jul. 20, 1988

[51] Int. Cl.$^5$ .............................................. A61M 5/32
[52] U.S. Cl. ..................................... 604/192; 604/263
[58] Field of Search ........................ 604/192, 187, 263

[56] References Cited

U.S. PATENT DOCUMENTS

| | | |
|---|---|---|
| 4,573,975 | 3/1986 | Frist et al. ........................... 604/192 |
| 4,596,562 | 6/1986 | Vernon . |
| 4,654,034 | 3/1987 | Masters et al. . |
| 4,717,386 | 1/1988 | Simmons . |
| 4,737,149 | 4/1988 | Gillilan . |
| 4,742,910 | 5/1988 | Staebler . |

Primary Examiner—John D. Yasko
Attorney, Agent, or Firm—Adrian D. Battison; Stanley G. Ade; Murray E. Thrift

[57] ABSTRACT

A shield device for use in sheathing a hypodermic needle includes a pair of flap members which are hinged to a central elongate narrow plate within which an open mouth of the sheath is defined. The flap members are hinged on either side of the central plate so that they can move from a retracted position lying parallel and on respective sides of the central sheath to a deployed position in which they form with the central plate a protective shield to hide fingers of the user from pricking as the needle is inserted into sheath. The flap members are retained in the retracted position by a simple latching arrangement which is released by compression of the flap members. The sheath and shield can be packaged as a disposable item in conventional manner with the disposable needle and needle base and can be used without modifying traditional handling techniques.

11 Claims, 2 Drawing Sheets

HYPODERMIC NEEDLE SHIELD

BACKGROUND OF THE INVENTION

This invention relates to a hypodermic needle shield.

Hypodermic needles are used in many fields and by medical, nursing, dental, veterinary and other personnel. Generally it is necessary after the use of a hypodermic needle to ensure that it is properly sheathed within a cylindrical container so that it is not exposed.

The need to resheath hypodermic needles in the protective guard or sheath currently available is well recognized. Principally the basis of this need is firstly to ensure that the needle is maintained in a clean or sterile condition when intermittent use is required and secondly to provide protection from accidental wounding or pricking of the operator and others nearby as may occur whenever a needle is left exposed outside moments of intended and actual use. Most unfortunately, the act of replacing a hypodermic needle in its guard or sheath is an occasion of particular risk for the operator since the sheath provides a small target at its open end and, if missed, stab wounding of the fingers is likely. This constitutes an extremely serious event in all instances where the needle tip is contaminated. Operator awareness of this personal risk moreover often means that the needles may be purposely left unsheathed.

In view of recent increased risks of contracting serious diseases by pricking with contaminated needles, hospitals often implement complex procedures to be undertaken whenever an inadvertent pricking or wounding of this type takes place. Even beyond hazards to the operator, therefore, there arises the serious loss of time which occurs in following the procedure whenever such an event takes place.

Conventionally a needle, its base for attachment to the required medical equipment, and a sheath surrounding the needle which connects to the base is supplied as a single packaged item for single time usage and then disposal as a throw away item. In all cases, however, it is necessary for the needle when used to be re-sheathed so that it cannot inadvertently protrude and cause pricking of an unsuspecting person.

Attempts have been made to design a shield device which can be used to protect the fingers of the operator when resheathing a needle.

U.S. Pat. Nos. 4,596,562 (Yernon), 4,737,149 (Gillilan) and 4,717,386 (Simmons) disclose arrangements in which a flat plate member includes an opening into which the sheath can initially be placed following which the needle is reinserted into the sheath while the hands of the operator are protected behind the flat plate.

U.S. Pat. No. 4,654,034 (Masters) discloses a modified shield in which there is provided a mouth of increased diameter with a conical portion leading into the shield so that the needle is better guided into the shield in the event of a slight inaccuracy by the operator.

U.S. Pat. No. 4,742,910 (Staebler) provides a needle sheath holder which includes a cylindrical hollow body into which the conventional sheath is inserted with suitable grip mechanisms being provided at the mouth of the cylindrical body. Surrounding the mouth is a flat plate type shield which is attached to the cylindrical body.

None of these devices has apparently achieved commercial success since in the field the problem remains unresolved. The reasons for the non-acceptance of the above proposals is not entirely clear but possibly this relates to the necessity of the additional devices of Yernon, Simmons, Gillilan and Staebler to modify the conventional handling techniques of the packaged and supplied disposable needle, needle sheath and needle base. These devices are not intended to be disposable or throw away items and thus must be removed from the sheath in a separate process thus reducing the efficiency of handling. The Masters device provides only limited protection since it merely increases the size of the mouth leaving the fingers still partly exposed to the danger of pricking and thus cannot be considered to be a satisfactory solution.

SUMMARY OF THE INVENTION

It is one object of the present invention, therefore, to provide an improved shield device for use with a hypodermic needle which enables the device to be used as a disposable item so that it can follow the conventional handling techniques used with the conventional sheaths currently available.

According to the invention, therefore, there is provided a shield device for use in sheathing a medical needle of the type comprising an elongate hollow needle and a base on which the needle is mounted, said shield device comprising a central body including a hollow cylindrical body portion defining an open mouth at one end into which the needle can be inserted so that it extends axially along the interior of the body portion with the base of the needle outside the open mouth, and a pair of flap members each mounted on the central body for pivotal movement about a hinge line adjacent to the open mouth and transverse to the cylindrical body portion a first retracted position in which the flap members lie substantially parallel on opposed sides of said cylindrical body portion to a second deployed position in which the flap members project outwardly from the hinge line to define in cooperation a protective plate surrounding said open mouth, and means for latching the flap members in the retracted position.

The invention thus provides a device which can be used to overcome or minimize the problems stated above. In particular the device can be manufactured as a disposable item which can be supplied in packaged form with the needle and needle base since the folded flap members in the retracted position enable the device to be readily packaged.

The initial packaged position with the flap members retracted allows the operator largely unobstructed visibility as is necessary for best needle selection. Color coding of the present invention offers the use of identifying data on the device and can assist the needle selection process.

Once selected the device provides the operator with an improved and flat needle container to grasp, in comparison with prior art cylindrically shaped needle sheaths. The needle base can be attached to the necessary syringe or other medical equipment in the conventional manner.

Preferably squeezing of the flap members alone is required to trigger the device to move to the deployed position as soon as the operator's finger grip is released. Thus no decision or conscious effort is involved beyond that which is conventional and long established and familiar with operators from the conventional prior art needle guards.

In the deployed position, the device offers ready advantage for resheathing of the needle. Left by itself, its larger than prior art dimensions mean that it is unlikely to be misplaced or lost; neither will it roll away. Placed on a level surface, moreover, the device elevates the opening for needle reinsertion to a convenient angle and view simplifying this action to a large extent compared to conventional needle sheaths. Alternatively if the operator chooses to grasp the present invention in one hand while resheathing the needle, this may be done easily and safely since the flap members provide the necessary protection.

In one embodiment, the cylindrical body can comprise simply a collar within which a conventional needle sheath is inserted. Thus the device is then manufactured as a separate unit preferably integrally molded from a suitable plastics material, and attached to the conventional needle sheath before packaging of the device, the needle sheath, needle and needle base as an individually supplied and disposable item. In an second embodiment, the needle sheath and the cylindrical body are formed as an integral construction for insertion of the conventional needle and needle base.

Preferably the flap members are biased to the deployed position by a steel coil spring which can be mounted upon a suitable hook on the side of the cylindrical body. Additional forces to bias the flap members to the deployed position can be provided by the molded hinges which retain sufficient memory to provide some biasing force. In addition the positioning of the operator's finger behind the flap members on the cylindrical body will act to provide a force moving the flap members to the deployed position so that in the unlikely event that the coil spring fails, the device remains operable with the need for only limited operator assistance.

The latch means is preferably of a type which maintains the flap members latched in the retracted position but is immediately released upon the operator squeezing the two flaps closer together while grasping the device thus increasing momentarily the nominal tension in the coil spring. Such squeezing is generally necessary to affix the needle base to its syringe or other medical attachment so that this conventional and normal action of the operator releases the latch mechanism so that as the needle and needle base are withdrawn, the flap members are automatically released into the deployed position.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
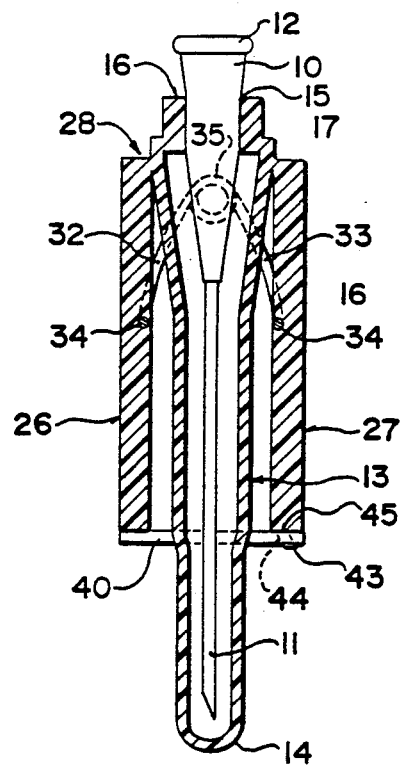
FIG. 1 is a cross sectional view showing a needle, needle base and needle sheath incorporating a shield arrangement in a retracted position thereof according to the invention.

In FIG. 1 there is shown a conventional needle assembly comprising a needle base 10 and a hollow hypodermic needle 11. The base includes the conventional screw lock flange 12 by which it can be attached to a suitable medical appliance for example a syringe. As these devices are of a conventional nature, they are not shown in detail.

In FIG. 1 the needle assembly is shown mounted within a sheath generally indicated at 13. The sheath comprises a hollow cylindrical body having a closed lower end 14 and an open mouth 15 so that the needle can be inserted into the hollow body to a position in which the needle base 10 cooperates as a press fit with an inner surface of the hollow body at the open mouth to hold the needle assembly in position within the sheath.

In the embodiment of FIG. 1, the sheath 13 is a continuous unitary body extending from the closed end 14 through to the open mouth 15. A portion 16 is flared slightly outwardly toward the open mouth so as to define shoulders 17 of increased transverse dimension relative to an end face 16 of the sheath.

Figure 2:
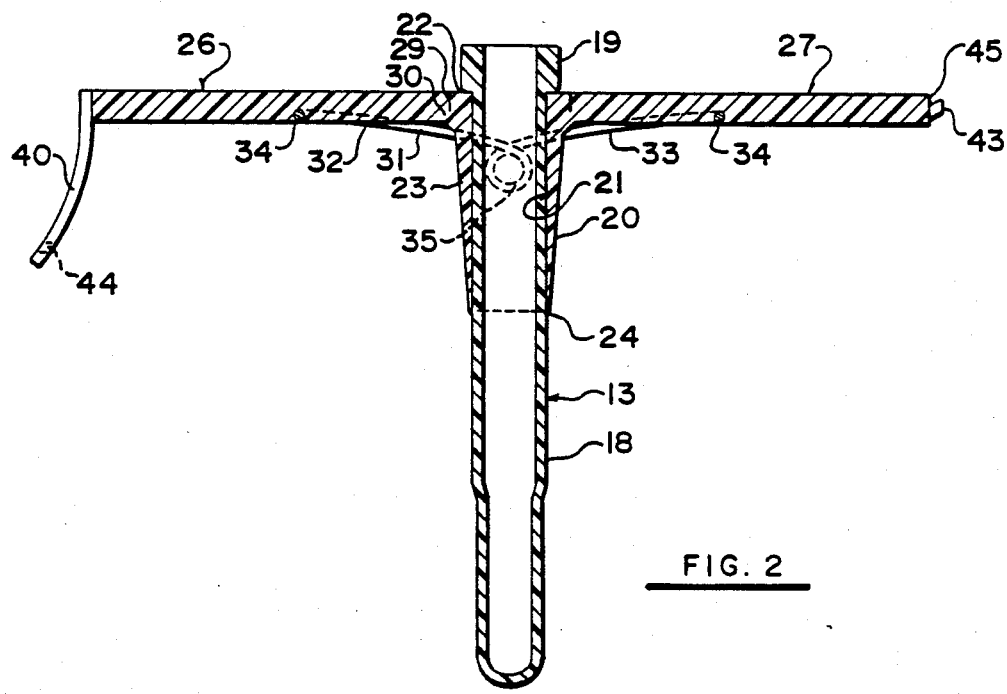
FIG. 2 is a cross sectional view similar to FIG. 1 of an alternative embodiment in which the needle sheath is separate from the shield device, the shield device being in the deployed position.

In FIG. 2 the sheath generally indicated at 13 is formed of two separate parts. Firstly there is provided a conventional sheath 18 which includes a cylindrical hollow body with a closed lower end as previously described which is substantially of constant diameter except for a flange 19 at an upper end. Such sheaths are entirely conventional. In this embodiment the conventional sheath 18 is received within a cylindrical receiving sleeve 20 which defines an inner surface 21 dimensioned to receive the outer surface of the sheath 18 as a sliding fit. The sleeve 20 includes an open end 22 against which the underside of the flange 19 sits. An outer surface of the sleeve 20 tapers as indicated at 23 toward a lower open end 24. The length of the sleeve 20 is less than that of the sheath 18 and the lower end 24 is open so that sheaths of different lengths can be received within the sleeve 20 depending upon requirements.

Figure 3:
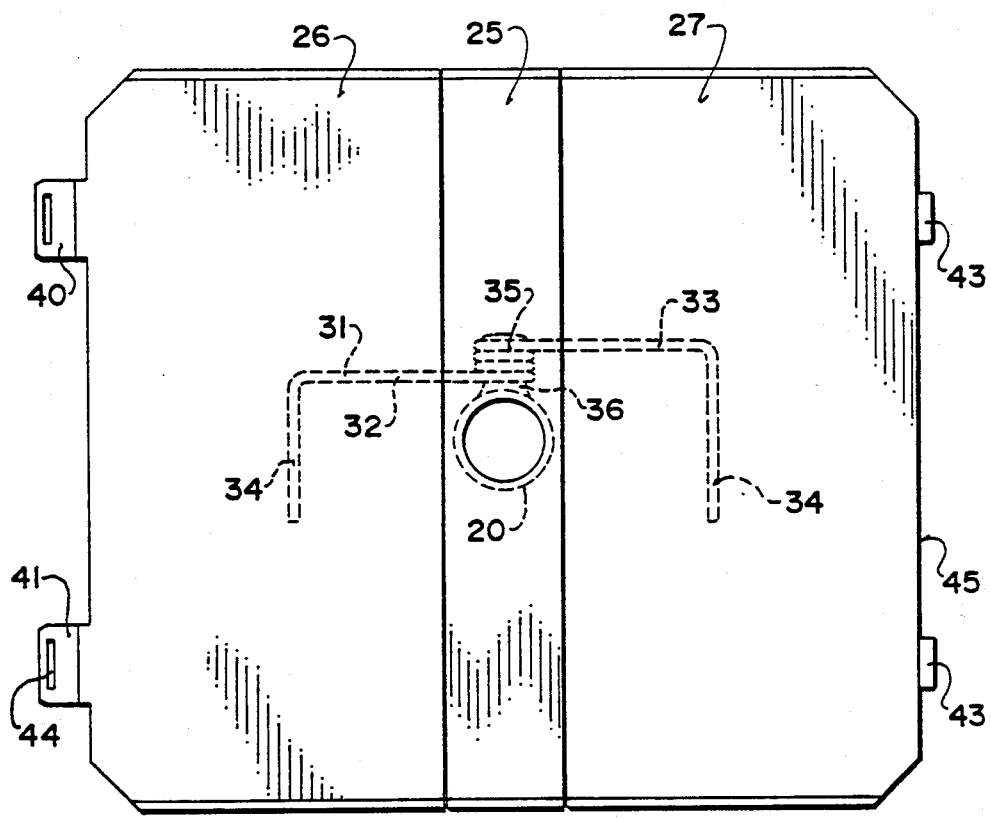
FIG. 3 is a top plan view of the shield device of FIG. 2 with the needle sheath removed.
Figure 4:
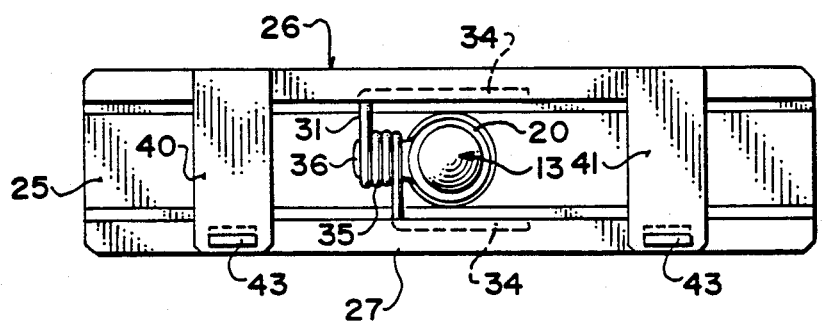
FIG. 4 is an underside view of the shield device of FIG. 3 in the retracted position.

For convenience of illustration only the embodiment of FIG. 2 is shown in the plan view of FIG. 3 and the underside view of FIG. 4 but it will be appreciated that the embodiment of FIG. 1 is substantially identical to that shown in FIGS. 3 and 4 except for the integrated construction of the sleeve and sheath.

As shown in FIGS. 3 and 4, the upper face 22 of the sleeve forms part of an elongate strip 25 which in the transverse direction shown in FIG. 2 is of only narrow width only slightly greater than the diameter of the open end of the sleeve 20. In the longitudinal direction shown in FIGS. 3 and 4, the plate 25 is elongated so as to form a length of the order of two to three inches. On either side of the central plate 25 is formed a respective one of a pair of flap members 26 and 27 each of which has a length equal to the length of the plate 25 and a width of the order of one to two inches. As shown in FIG. 3, in the deployed position, the flap members 26 and 27 cooperate with the plate 25 to form a substantially rectangular shield plate. The shape of the outer edges can be varied to provide various esthetic effects and the upper surface can include a design or pattern again for an attractive appearance. The dimensions of the plate are therefore of the order of two to four inches in width and length.

The flap members 26 and 27 are attached to the central plate 25 by molded hinge members 28 which are formed by molding a cut line 29 shown in FIG. 2 leaving a small section 30 of the plastics material from which the device is molded which is sufficiently thin to allow flexing of the flap members about the hinge line defined by the material 30 while providing sufficient strength at that point to avoid tearing of the flap members from the central plate. The device can be molded so that the plastics material retains a memory tending to return the flap members to the deployed position shown in FIGS. 2 and 3.

A spring 31 provides a biasing force on the flap members tending to move them to the deployed position shown in FIG. 2. Thus the spring 31 includes a pair of spring arms 32 and 33 each of which includes a right angle portion 34 for engaging an under surface of the respective flap member. From the right angled portion, each arm extends inwardly to a central coil section 35 which is mounted upon a projection or nose 36 molded onto the outer surface of the sleeve 20. The projection 36 thus provides a fixed support for the coil 35 which is torsioned to bias the arms 32 and 33 outwardly from the retracted position shown in FIG. 1 toward the deployed position shown in FIG. 2. The spring can be applied into the mold during the molding of the device so that it is attached and integrated with the unit in the molding process.

A latching arrangement is provided to hold the flap members in the retracted position as shown in FIGS. 1 and 4. The latching arrangement comprises a pair of straps 40 and 41 which are attached to one edge of the flap member 26 remote from the hinge line thereof. The straps 40, 41 are integrally molded with the flap member 26 and are molded so as to have a memory tending to spring them away from a position at right angles to the flap member to the position illustrated in FIG. 2. In the latched position, each of the straps 40, 41 cooperates with a male projection 43 provided on the edge of the other flap member 27. Thus in the retracted position shown in FIG. 1, the male member 43 projects downwardly and it is also inclined in a direction away from the other flap member so that it can cooperate with an opening 44 provided in the strap 40, 41 to hold the flap members in the retracted position shown. As the flap members are under spring tension tending to move them apart, out of the retracted position, the inclination of the male member 43 away from the other flap member tends to pull the edge of the opening 44 into the Y-shaped area between the male member 43 and the outer edge 45 of the flap member 27. The sides of the opening 44 can be inclined in the same direction as the projecting male member 43 so as to cooperate in retaining the latched position.

In operation, the device in the retracted latched position shown in FIGS. 1 and 4 is assembled with the needle assembly (and the separate sheath in the embodiment of FIGS. 2, 3 and 4) so as to form the complete assembly as shown in FIG. 1. The completed assembly is then packaged in suitable materials generally of a transparent nature to allow inspection of the contents for needle selection. When the needle is required for use, the packaging is opened and the assembly removed for use. During the use, the sides of the flap members are grasped by the operator so that the needle base can be attached by the flange 12 to the required medical equipment. The shield and flap members are then pulled away from the needle so that the needle is removed from the sheath for use. The squeezing effect necessary to complete the attachment of the needle base to the equipment and to remove the needle from the sheath is sufficient to cause the flap members to move more closely together at the ends thereof remote from the hinge lines. As the edge of the flap member 27 moves toward the flap member 26, the edges of the opening 44 force the opening away from the projecting male member 43 so that it is released from the male member and allowed to spring open away from the edge of the flap member 27 under the spring force to take up the outwardly extended position at an angle slightly greater than right angles as shown in FIG. 2. Subsequent release of the compression of the flap members by the operator then allows the flap members to move to the deployed position shown in FIG. 2 under the spring force provided by the spring 31 and by the memory in the molded plastics material and, if necessary, by finger force provided on the rear of the flap members by the operator's fingers grasping the device behind the flap members.

When deployed therefore the shield and sheath assembly can simply be placed upon a suitable surface and left to stand without any danger of it rolling away or being misplaced in view of its relatively large dimensions.

When the use of the needle in a complete, the needle can be returned to its sheathed position. In one mode of operation, the device can be left sitting on the surface with one edge of the shield defined by the flap members 26, 27 and the central plate 25 resting upon the surface with a further point of contact on the surface being provided by the lower end 14 of the sheath. This inclines the sheath away from the surface so that the needle can simply be placed into the sheath without the necessity for the operator to touch the sheath and shield assembly. In a further mode, the operator can grasp the sheath and shield assembly at the sheath behind the shield so that the shield plate protects the fingers of the user as the needle is moved toward the open mouth of the sheath.

The device is intended as a disposable device so that when the needle has been used and resheathed, the whole unit is thrown away for disposal leaving the flap members in the deployed position.

Since various modifications can be made in my invention as hereinabove described, and many apparently widely different embodiments of same made within the spirit and scope of the claims without departing from such spirit an scope, it is intended that all matter contained in the accompanying specification shall be interpreted as illustrative only and not in a limiting sense.

I claim:

1. A shield device for use in sheathing a medical needle of the type comprising an elongate hollow needle and a base on which the needle is mounted, said shield device comprising a central body including a hollow cylindrical body portion defining an open mouth at one end into which the needle can be inserted so that it extends axially along the interior of the body portion with the base of the needle outside the open mouth, a shield members having a central strip portion with two parallel sides and having a width between the sides at least equal to the width of the cylindrical body portion and a length such that the strip portion extends outwardly from the central body to respective sides thereof and two flat flap members each mounted on the central strip portion for pivotal movement about a hinge line along a respective side of the central strip portion adjacent to the open mouth from a first retracted position in which the flap members lie substantially parallel on opposed sides of said cylindrical body portion to a second deployed position in which the flap members project outwardly from the central strip portion, the two flap members and the central strip portion being shaped to define in cooperating a protective plate fully surrounding said open mouth, and means for latching the flap members in the retracted position.

2. The invention according to claim 1 including means biasing the flap members to the deployed position and wherein the latching means is arranged such that it is released to allow said movement to the deployed position by manual squeezing of said flap members in a direction away from said deployed position.

3. The invention according to claim 1 wherein the flap members are formed from a material which is resistant to needle penetration.

4. The shield device according to claim 1 wherein the central body and the flap members are integrally molded from a plastics material.

5. The invention according to claim 4 including a separate metal spring member biasing said flap members to said deployed position.

6. The invention according to claim 1 wherein the latch means comprises at least one strap member mounted on one of said flap members at a position thereon spaced from said hinge line and means on the other of the flap members for releasibly engaging said strap member in the retracted position with the strap member extending across the space defined between said parallel flap members in the retracted position.

7. The invention according to claim 6 wherein the latch means comprises a pair of strap members each arranged to project from an edge of one of the flap members spaced from the hinge line thereof such that each of the straps members can extend from the associated flap member to the other of the flap members with each being arranged on a respective side of the cylindrical body portion.

8. The shield device according to claim 1 wherein the cylindrical body portion comprises an outer sleeve and a separate cylindrical needle sheath inserted as a sliding fit within the outer sleeve.

9. The invention according to claim 8 wherein the outer sleeve includes an end opposite said open mouth which is open and through which the needle sheath extends.

10. A disposable hypodermic needle assembly comprising an elongate hollow needle, a base on which the needle is mounted, a cylindrical needle sheath having an open mouth at one end for receiving the needle fed therein and for cooperating with the needle base to hold the needle in place, and a shield device comprising a central body including a hollow cylindrical sleeve portion into which the sheath is inserted as a sliding fit, and a shield members having a centrals trip portion with two parallel sides and having a width between the sides at least equal to the width of the cylindrical body portion and a length such that the strip portion extends outwardly from the central body to respective sides thereof and two flat flap members each mounted on the centrals trip portion for pivotal movement about a hinge line along a respective side of the central strip portion adjacent to the open mouth of the sheath from a first retracted position in which the flap members lie substantially parallel on opposed sides of said cylindrical body portion to a second deployed position in which the flap members project outwardly from the central strip portion, the two flap members and the central strip portion being shaped to define in cooperating a protective plate fully surrounding said open mouth spring means biasing said flap members to said deployed position and means for latching the flap members in the retracted position, said central body, central strip portion and flap members being integrally molded from a plastics material.

11. A disposable hypodermic needle assembly comprising an elongate hollow needle, a base on which the needle is mounted, and a needle sheathing and shield device comprising a central body including a hollow cylindrical body portion defining an openmouth at one end into which the needle can be inserted so that it extends axially along the interior of the body portion with the base of the needle cooperating with the open mouth to retain the needle in position, a shield members having a central strip portion with two parallel sides and having a width between the sides at least equal to the width of the cylindrical body portion and a length such that the strip portion extends outwardly from the central body to respective sides thereof and two flat flap members each mounted on the central strip portion for pivotal movement about a hinge line along a respective side of the central strip portion adjacent to the open mouth from a first retracted position in which the flap members lie substantially parallel on opposed sides of said cylindrical body portion to a second deployed position in which the flap members project outwardly from the central strip portion, the two flap members and the central strip portion being shaped to define in cooperation a protective plate fully surrounding said open mouth, means biasing said flap members to the deployed position and means for latching the flap members in the retracted position, said central body portion and said flap members being integrally molded from a plastics material.

* * * * *